United States Patent [19]

Hi-Hwa Yuan et al.

[11] Patent Number: 4,625,544
[45] Date of Patent: Dec. 2, 1986

[54] DETERMINING SATURATION AND PERMEABILITY USING MERCURY CAPILLARY PRESSURE CURVES

[75] Inventors: Herbert Hi-Hwa Yuan; Benjamin F. Swanson; Robert G. Stapleton, all of Houston, Tex.

[73] Assignee: Shell Oil Company, Houston, Tex.

[21] Appl. No.: 823,548

[22] Filed: Jan. 29, 1986

Related U.S. Application Data

[63] Continuation of Ser. No. 727,462, Apr. 26, 1985, abandoned.

[51] Int. Cl.[4] ............................................ G01N 15/08
[52] U.S. Cl. ........................................................ 73/38
[58] Field of Search ............................................. 73/38

[56] References Cited

U.S. PATENT DOCUMENTS

| | | | |
|---|---|---|---|
| 2,604,779 | 7/1952 | Purcell | 73/38 |
| 2,641,924 | 6/1953 | Reichertz | 73/38 |
| 3,388,586 | 6/1968 | Golmard et al. | 73/38 |
| 3,859,843 | 1/1975 | Lowell | 73/38 |
| 3,882,714 | 5/1975 | Libal et al. | 73/38 |
| 4,170,129 | 10/1979 | Lowell et al. | 73/38 |
| 4,203,317 | 5/1980 | Gupta | 73/38 |
| 4,211,106 | 7/1980 | Swanson | 73/38 |

*Primary Examiner*—Michael J. Tokar
*Assistant Examiner*—Joseph W. Roskos

[57] ABSTRACT

A method using mercury capillary pressure curves for determining various characteristics of formations. The mercury capillary pressure curve is amplified and small changes are used to compute residual saturation, permeability, Archie's exponent m and the resistivity factor F of the formation.

14 Claims, 3 Drawing Figures

DETERMINING SATURATION AND PERMEABILITY USING MERCURY CAPILLARY PRESSURE CURVES

This is a continuation, of application Ser. No. 727,462, filed Apr. 26, 1985, now abandoned.

BACKGROUND OF THE INVENTION

The present invention relates to a method and apparatus for determining the characteristics of reservoir rocks and particularly, the characteristics of core samples that are removed from reservoir rocks.

One method that has been used for determining the characteristics of reservoir rocks is the measurement of capillary pressure. In particular, the mercury capillary pressure response of the reservoir rock has been measured from which estimates have been made of the permeability of the rock as well as the pore volume. One mercury capillary pressure method and apparatus is described in U.S. Pat. No. 2,604,779. In this method the rock sample or core is placed in a closed vessel, the vessel is evacuated and then partially filled with mercury to cover the core. Mercury is then forced into the vessel at a constant pressure while plotting the volume of mercury versus the pressure in the vessel. This provides a plot of the mercury capillary pressure versus volume of the core from which various core characteristics may be determined. For example, total pore volume and an indication of the permeability of the core can be determined.

In an article appearing in the Journal of Geophysical Research, Volume 71, No. 12, June 15, 1966, at pp. 2911, entitled "Flow of Fluids Through Porous Mediums", there is described experiments with air/water interfaces moving through simple synthesized permeable specimens. The authors observed that the interface did not move continuously through the synthesized sample but rather in a non-continuous manner from pore to pore. The abrupt movements of the interface resulted in pressure drops in the pressure measured in the sample holder.

While the authors observed the non-continuous manner in which the interface moved through the synthetic permeable specimen, they did not utilize actual rock samples. Furthermore, they relied upon air/water interfaces. For the results to be useful the interface must be conventional water/oil interface that occurs in reservoir rocks or mercury/air interface. Further, the pores that occur in reservoir rocks are smaller than those present in the authors' synthetic sample by a factor of at least 10 to 100. The equipment and procedures used by the authors would be incapable of measuring the pressure and volume changes occurring in an actual rock sample.

SUMMARY OF THE INVENTION

The present invention is based on the discovery that by using extremely slow injection rates and making accurate measurements of both the volume and pressure of the displacing fluid that is injected, one can detect the pressure at which the displacing fluid breaks through to each subison pore system in the rock sample. The invention utilizes these measurements of the volumes of subison pore systems to yield the saturation of the non-wetting phase in the rock sample and the residual saturation from a given initial saturation. The data also is utilized to predict the absolute permeability of the sample as well as the value of Archie's exponent m and the formation resistivity factor F used in Archie's equations that have, since 1942, been used to calculate oil and/or water saturations in clean sands. Archie's original empirical relations were modified by Waxman-Smits equations described in "Electrical Conductivity in Oil-Bearing Shaly Sands", Waxman-Smits, 1968 SPE Journal, June, pp. 107–122. Both the Archie and the Waxman-Smits equations require determination of the formation resistivity factor F and Archie's exponent m.

The apparatus of the present invention is an improvement over that previously used in that it permits very slow controlled injection rates in combination with means for accurately measuring both the injected volumes and pressures. Further, the sample holder has been modified to provide a leak-tight vessel without the use of gaskets or other sealing means. The elimination of gaskets removes a large source of error in previous equipment used for making capillary pressure measurements.

BRIEF DESCRIPTION OF THE DRAWINGS

The present invention will be more easily understood from the following detailed description of the preferred embodiment when taken in conjunction with the attached drawings in which.

DESCRIPTION OF PREFERRED EMBODIMENT

Figure 1:
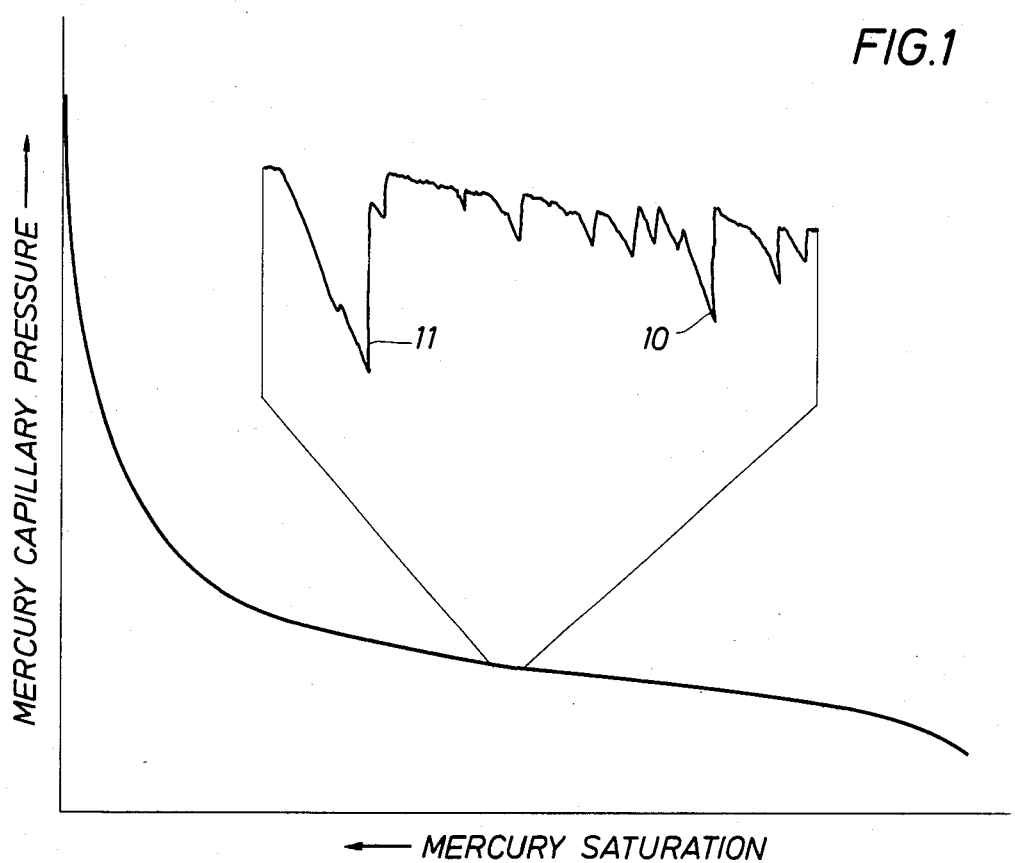
FIG. 1 is a typical capillary pressure plot with a portion of the curve enlarged.
Figure 2:
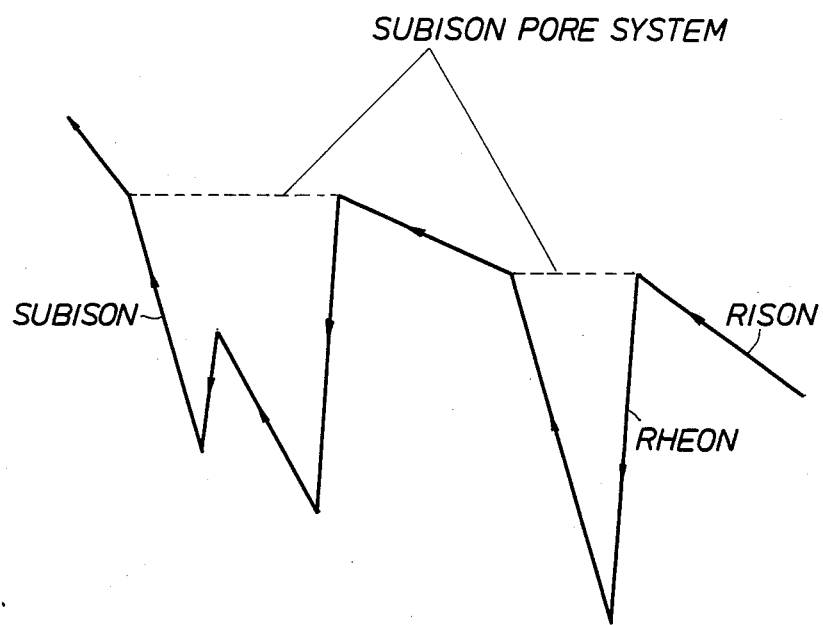
FIG. 2 is the portion of the curve that is enlarged in FIG. 1 shown to a larger scale.

Referring now to FIGS. 1 and 2, there is shown a mercury capillary pressure curve and a portion of the curve enlarged. In FIG. 1 the mercury saturation increases to the left while the mercury capillary pressure increases in a "Y" direction. This is a typical curve from a formation rock, for example, of Berea sandstone and shows for low saturations, the pressure increases very slowly but with increasing mercury saturation the pressure increases rapidly. Also shown in FIG. 1 is an enlargement of a small portion of the curve showing the pressure drops 10 and 11. The pressure drops are the result of the mercury passing through the throat of a pore and flowing into the pore space. As the mercury flows into the pore space the pressure decreases rapidly until the pore starts to fill at which time, the pressure then increases at a steady rate to approximately its initial value before breaking through the throat of the pore. The enlarged portion of FIG. 1 is shown to an even larger scale in FIG. 2 where the various portions of the curve are labeled. In particular, the rising portion of the capillary pressure curve to previously unattained levels is referred to as a rison. On the other hand, the rising portion of the capillary pressure curve to previously attained levels is referred to as a subison, while the decreasing pressure portion of the curve is referred to as a rheon. The volume between the point at which the pressure initially decreases and the point at which it again achieves its original value is the volume of a subison pore system. A subison pore system consists of only a rheons and subisons. If the horizontal distance of each pore system were summed, one would obtain the volume of the pore system of the sample or more particularly the trapping pore volume. The trapping pore volume is the volume of the pore system that can hold hydrocarbons after waterflooding.

From the above description it can be seen that the trapped saturation of the non-wetting phase $S_{nwr}$ fluid after a waterflood can be predicted from the following equation:

$$S_{nwr} = \frac{V_{sT}}{V_p} \quad (1)$$

where $V_{sT}$=total subison pore system volume and $V_p$=total pore volume of sample.

The above relationship holds true for any strongly water-wet system which would be present after a waterflood type of recovery. One could also predict the residual saturation $S_r$ if one knows the initial saturation $S_I$ by summing the volume of all the given subison pore systems, that would be saturated at an initial saturation of $S_I$.

$$S_r = \sum_{S \leq S_I} \frac{S_v}{V_p} \quad (2)$$

where $S_v$=the volume of a single subison pore system and $S_I$=initial saturation.

Similarly the permeability K of the formation can be derived from the following expression:

$$k = 477 \phi \sum_{i}^{N_r} \frac{V_{ri}}{V_{rT}} \frac{1}{p_r^2} \quad (3)$$

where
$\phi$=porosity of the sample
$N_r$=number of measured risons
$V_{ri}$=volume of a given rison
$V_{rT}$=total volume of risons
$P_r$=entry pressure of rison The model equations for the permeability are derived by recognizing that the distribution of risons governs the flow of fluid, i.e. permeability. Each rison can be considered as a capillary tube of a diameter equal to the entry diameter (which can be calculated from the entry pressure) and with a volume equal to the rison volume. Thus, the permeability can be determined from the distribution of risons represented as capillary tubes in parallel over a wide range of different diameters.

Likewise, the Archie's exponent m and the formation resistivity factor F can be calculated from the following equations:

$$m = \frac{1 + \log[V_{rT}/2 V_p]}{\log \phi} \quad (4)$$

$$F = \frac{2V_p}{\phi V_{rT}} \quad (5)$$

These equations for m and F are calculated, as with the permeability, from the risons represented as capillary tubes in parallel. The total conductivity is then the sum of the conductivities from each tube. The angular dependence disappears because each rison is assumed to have an isotropic contribution. Thus, the sum of the conductivities amounts by cancellation to just the total rison volume, $V_{rT}$.

The average pore volume can be calculated from the following expression:

$$\bar{S}_v = \frac{V_{sT}}{N_s} \quad (6)$$

where $N_s$=number of subison pore systems.

All of the above data can be obtained from accurate measurements of the volumes and the pressures during a single capillary pressure measurement using the apparatus of this invention. For example, if the core is first evacuated and then mercury forced through the core until it is completely saturated to obtain a complete mercury capillary pressure curve, both the total pore volume as well as the volume of each subison will be obtained. The pressure is measured with an accuracy of better than 1 part in $10^4$, using a 16-bit analog-to-digital converter, while the volume is measured with an accuracy of 1 part in $10^6$ and the measured values converted to a digital quantity, the required calculations can be performed in a small computer or specialized processor. Since the measurements are in digital form, it will be a simple matter for the processor to detect a decrease in pressure indicating a rheon as shown in FIG. 2. The processor can sum the volume until the pressura again reaches the value it had at the time that it entered the pore space to determine the total volume of all the subisons. The remaining calculations can then be readily performed.

Figure 3:
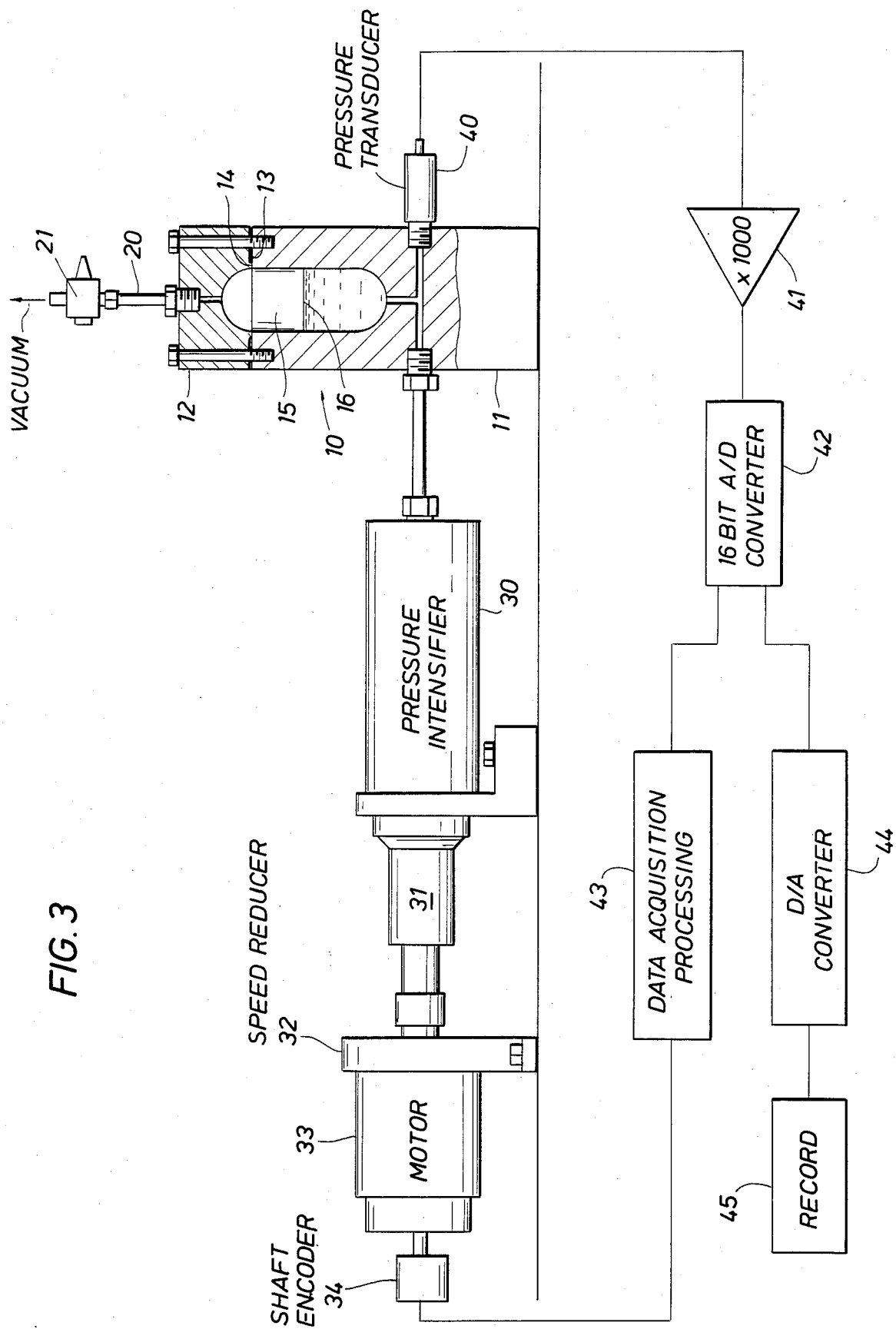
FIG. 3 is a block diagram of an apparatus suitable for performing the present invention.

Referring to FIG. 3, there is shown an instrument suitable for carrying out the above measurements with the accuracy required. In particular, there is shown a sample holder 10 which is formed of two cup-shaped members 11 and 12. The mating surfaces 13 and 14 of the cup-shaped surfaces are ground and lapped so that they will form a fluid-tight seal without the addition of any sealing material or gaskets. The presence of gaskets or sealing material will produce faulty results since the voids in gaskets, such as O-rings, or sealing materials can contribute to the volume of the pore spaces that are being measured. In order to effect the seal between the two mating surfaces, the two units should be bolted together with the tension on the bolts being accurately measured as by means of torque wrenches or similar devices. The sample holder is provided with a line 20 and a valve 21 which is coupled to a source of suitable vacuum. This permits the sample holder and the core material to be completely evacuated before the measurements are started. Prior to evacuating the chamber and the core material the chamber should be filled to a level 16 with a fluid which is to be used to obtain the capillary pressure curve.

A pressure intensifier 30 is used for applying pressure to the fluid used in the capillary pressure measurements. The pressure intensifier is preferably a positive displacement piston type, pump which is driven by actuating means 31. Preferably, the actuating means takes the rotary motion from the speed reducer 32 and converts it to linear motion for driving the piston of the pump unit. The speed reducer in turn is driven by a synchronus motor 33 whose rotation is determined by a shaft/encoder 34. The speed reducer should have a speed reduction of approximately 1000 to 1 when using the conventional 3600 rpm motor and the actuating means 31 should convert this rotary motion into a linear movement of the piston that provides a fluid displacemment of approximately $1 \times 10^{-5}$ cc/sec. or less. The pressure in the sample holder is detected by a pressure transducer 40 having an accuracy of better than 1 part in $10^4$ with the signal being amplified by an amplifier 41 up to 1000 times. The amplified signal is supplied to a 16-bit analog-to-digital converter 42 which converts the analog signal to a related digital signal. The digital signal is supplied to both a data acquisition and processing unit 43 as well as to a digital-to-analog converter 44 whose signal is recorded on a chart recorder 45. In particular, the digital-to-analog converter 44 uses only the first 10 bits of the data word from the converter 42 for display on the chart recorder. In particular, the 10-bit signal is displayed full scale on the chart recorder and upon the occurrence of the 11th bit in the data word from the converter 42, the converter 44 resets the chart recorder to 0 so that it can again be used full scale for displaying the first 4 bits of the analog-to-digital converter 42. This, in effect, provides an accuracy of 1 in 65,000 for the data recorded on the recorder 45. The data acquisition processing unit 43 also receives data from the shaft encoder 34 and can make the calculations described above. In particular, the shaft encoder should provide an output signal related to the position of the motor shaft which when correlated with the volume supplied by the pressure intensifier 30 provides an overall accuracy of at least 1 part in $10^6$.

This system is operated in much the same manner as the system described in the patent referred to above. In particular, the sample holder is opened and the core material or other sample placed in the sample holder and the sample holder then assembled. The sample holder is partially filled with a displacing fluid, for example mercury, and then evacuated through line 20. After evacuation, the pressure on the the mercury is increased by the intensifier 30 while the measurements are made. Once the measurements are obtained, the various characteristics of the core material described above can be readily computed.

What is claimed is:

1. A method for determining a preselected characteristic of a porous body, comprising:
    confining a portion of said body in a closed zone,
    evacuating said zone and pore spaces of said body to a high vacuum,
    admitting a fluid into said zone to a level above said body to completely immerse said body in said fluid and fill said zone with said fluid,
    continuously injecting additional fluid into said zone at a preselected rate,
    substantially continuously noting pressure changes of said fluid in said zone and the volume of fluid injected into said zone,
    determining rheons, subisons and risons from said noted pressure changes and injected volumes, and
    determining said preselected characteristic of said body from said noted pressure changes, said noted injected volumes, said determined rheons, said determined subisons, or said determined risons, or from combinations thereof.

2. A method for determining a capillary pressure curve for a porous body, comprising:
    confining a portion of said body in a closed zone,
    evacuating said zone and pore spaces of said body to a high vacuum,
    admitting a non-wetting fluid into said zone to a level above said body to completely immerse said body in said fluid and fill said zone with said fluid,
    continuously injecting additional fluid into said zone at a preselected rate,
    substantially continuously noting pressure changes of said fluid in said zone corresponding to the volume of fluid injected into said zone,
    determining subisons and risons from said noted pressure changes and injected volumes, and
    determining said capillary pressure curve from said determined subisons, risons and noted pressure changes.

3. A method for resolving pore spaces in a porous body, comprising:
    confining a portion of said body in a closed zone,
    evacuating said zone and pore spaces of said body to a high vacuum,
    admitting a non-wetting fluid into said zone to a level above said body to completely immerse said body in said fluid and fill said zone with said fluid,
    continuously injecting additional fluid into said zone at a preselected rate,
    substantially continuously noting pressure changes of said fluid in said zone corresponding to the volume of fluid injected into said zone,
    determining subisons and risons from said pressure changes and injected volumes, and
    determining said resolved pore spaces from said determined subisons and risons.

4. A method for determining characteristics of a porous body, comprising:
    confining a portion of said body in a closed zone,
    evacuating said zone and pore spaces of said body to a high vacuum,
    admitting a non-wetting fluid into said zone to a level above said body to completely immerse said body in said fluid and fill said zone with said fluid,
    continuously injecting additional fluid incrementally into said zone at a preselected rate, and
    substantially continuously determining subisons and risons.

5. A method as described in claim 4, wherein said characteristic is residual saturation, and further comprising:
    measuring the total pore volume of said body.

6. A method as described in claim 4, wherein said characteristic is residual saturation, and further comprising:
    determining the initial saturation of said body.

7. A method as described in claim 4, wherein said characteristic is permeability, further comprising:
    measuring the entry pressure for each rison of said body.

8. A method as described in claim 4, wherein said characteristic is Archie's lithological exponent, m, for said body.

9. A method as described in claim 4, wherein said characteristic is the resistivity factor, F, of said body.

10. Apparatus for determining characteristics of a porous body, comprising:
    sample holder formed from two cup-shaped members detachably secured together to create a hollow holder for containing in said holder, said body, with the mating surfaces of said two cup-shaped members having ground surfaces to form a leaktight seal therebetween,
    positive displacement pump interconnected with said sample holder for injecting a fluid into said holder,
    drive means interconnected with said pump to provide a preselected flow rate into said sample holder, first means interconnected with said pump for determining the volume of fluid injected into said holder by said pump, second means interconnected with said sample holder, for measuring the pressure therein, and processing means for analyzing data from said first and second means to determine said characteristics.

11. The apparatus as described in claim 10, wherein said first means has an accuracy of at least 1 part in $10^6$.

12. The apparatus as described in claim 10, wherein said second means has an accuracy of at least 1 part in $10^4$.

13. The apparatus as described in claim 10, and further comprising:

recording means for recording data from said first and second means.

14. The apparatus as described in claim 10, wherein said drive means operates to provide a flow rate less than about $1 \times 10^{-5}$ cubic centimeters per second.

* * * * *